(12) United States Patent
Freund et al.

(10) Patent No.: US 6,491,897 B1
(45) Date of Patent: Dec. 10, 2002

(54) STABLE PHARMACEUTICAL BUDESONIDE PREPARATION FOR PRODUCING PROPELLANT-FREE AEROSOLS

(75) Inventors: Bernhard Freund, Gau-Algesheim; Michael Krueger, Ingelheim; Bernd Zierenberg, Bingen, all of (DE)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/396,673

(22) Filed: Sep. 9, 1999

Related U.S. Application Data

(63) Continuation of application No. 08/473,921, filed as application No. PCT/EP96/02700 on Jun. 21, 1996, now abandoned.

(30) Foreign Application Priority Data

Jun. 27, 1995 (DE) .......................... 195 23 207

(51) Int. Cl.⁷ ................................. A61K 9/12
(52) U.S. Cl. ........................ 424/45; 424/46
(58) Field of Search ................... 424/45, 46

(56) References Cited

U.S. PATENT DOCUMENTS

| | | | |
|---|---|---|---|
| 4,450,151 A | | 5/1984 | Shinozawa |
| 4,615,699 A | | 10/1986 | Gale et al. |
| 4,857,312 A | | 8/1989 | Hegasy et al. |
| 4,919,919 A | | 4/1990 | Aouda et al. |
| 5,047,230 A | | 9/1991 | Nagy et al. |
| 5,136,124 A | | 8/1992 | Cronin et al. |
| 5,225,183 A | * | 7/1993 | Purewal et al. |
| 5,370,862 A | | 12/1994 | Klokkers-Bethke et al. |
| 5,736,124 A | * | 4/1998 | Akehurst et al. |
| 5,776,432 A | * | 7/1998 | Schultz et al. |
| 5,914,122 A | * | 6/1999 | Otterbeck et al. |
| 5,958,378 A | * | 9/1999 | Waldrep et al. |
| 6,004,537 A | * | 12/1999 | Blondino et al. |
| 6,039,932 A | * | 3/2000 | Govind et al. |

FOREIGN PATENT DOCUMENTS

| | | |
|---|---|---|
| DE | 3246081 | 6/1984 |
| DE | 4123663 | 1/1993 |
| EP | 0 234 500 | 9/1987 |
| EP | 0310910 | 12/1989 |
| EP | 605578 * | 7/1994 |
| GB | 970027 | 9/1964 |
| JP | 61-83117 | 4/1986 |
| WO | 8203172 | 9/1982 |
| WO | WO 90/06750 | 6/1990 |
| WO | 92/06675 | 4/1992 |
| WO | 93 05765 | 4/1993 |
| WO | WO 9315715 | 8/1993 |
| WO | WO 93/15741 | 8/1993 |
| WO | WO 94/13262 | 6/1994 |
| WO | 96 19969 | 7/1996 |

OTHER PUBLICATIONS

Patent Abstracts of Japan, vol. 5, No. 136 (C–69)[808], 28th Aug. 1981; & JP–A–56 71 046 (Nippon Kayaku K.K.) 13–06–1981.

* cited by examiner

*Primary Examiner*—Raj Bawa
(74) *Attorney, Agent, or Firm*—Robert P. Raymond; Mary-Ellen M. Devlin; Alan R. Stempel

(57) ABSTRACT

A stable ethanolic solution of budesonide is disclosed, which solution is suitable for use in nebulizers, together with a process for making such stable solution.

43 Claims, No Drawings

STABLE PHARMACEUTICAL BUDESONIDE PREPARATION FOR PRODUCING PROPELLANT-FREE AEROSOLS

This aplication is a continuation of 08/973,921 Feb. 3, 1998 ABN which is a 371 of PCT/EP96/02700 Jun. 21, 1996.

The present invention relates to pharmaceutical preparations in the form of stable ethanolic solutions of active substances for producing propellant-free aerosols.

In the last 20 years, the use of metering aerosols has become an established component of the treatment of obstructive lung diseases, particularly asthma. Usually, fluorochlorohydrocarbons have been used as propellant gases. Since the ozone-damaging potential of these propellant gases was recognised, more and more efforts have been made to develop alternatives. One alternative is the development of nebulisers in which aqueous solutions of pharmacologically-active substances are sprayed under high pressure so as to produce a mist of inhalable particles. The advantage of these nebulisers is that there is no need to use any propellant gases whatsoever.

Some nebulisers are described, for example, in PCT Patent Application WO091/14468, the contents of which are referred to hereinafter. In the nebulisers described therein, solutions of defined volumes containing active substances are sprayed, using high pressures through small nozzles so as to produce inhalable aerosols with a preferred particle size of between 1 and 10, preferably between 2 and 5 micrometers.

Hitherto, it has been assumed that, with conventional metering aerosols containing propellant gas, the optimum level of lung-bound particles is obtained in the aerosol. It has now been found, surprisingly, that by using ethanolic active substance solutions in combination with, for example, the above-mentioned nebulisers it is possible to generate a significantly better spectrum of inhalable particles than is usually the case with metering aerosols which contain propellant gas.

Suitable solvents for the pharmaceutical preparation within the scope of the present inventions are solutions containing at least 70% (v/v) of ethanol; solutions containing at least 85% (v/v) are preferred whilst solutions having an ethanol content of more than 95% (v/v) are particularly preferred. The concentration is given in percent by volume (v/v), the remainder being water. Most particularly preferred is ethanol which already contains small amounts of water, e.g. 96% ethanol, so that it is no longer hygroscopic and evaporates azeotropically.

Apart from water, the solvent may include other cosolvents and the pharmaceutical preparation may also contain flavourings and other pharmacological excipients. Examples of cosolvents are those which contain hydroxyl groups or other polar groups, e.g. alcohols, especially isopropyl alcohol, glycols, particularly propylene glycol, polyethylene glycol, polypropylene glycol, glycol ether, glycerol, polyoxyethylene alcohols and esters of polyoxyethylene fatty acids. Cosolvents are suitable for increasing the solubility of the excipients and possibly the active substances.

The proportion of dissolved pharmaceutical substance in the finished pharmaceutical preparation is between 0.001 and 5%, preferably between 0.05 and 3%, most particularly 0.01 to 2%, where the figures refer to the percentage by weight. The maximum concentration of pharmaceutical substance depends on the solubility in the solvent and on the dosage required to achieve the desired therapeutic effect.

As pharmaceutically active agent in the new preparations, it is possible to use any substances which are suitable for administration by inhalation and which are soluble in the solvent specified. These may include, in particular, betamimetics, anticholinergics, antiallergics, PAF-antagonists and particularly steroids and combinations of active substances thereof.

The following are mentioned specifically by way of example:

Tiotropium bromide, 3-[(hydroxydi-2-thienylacetyl)oxy]-8,8-dimethyl-8-azoniabicyclo[3,2,1]oct-6-en-bromide As betamimetics:

| | | | |
|---|---|---|---|
| Bambuterol | Bitolterol | Carbuterol | Formoterol |
| Clenbuterol | Fenoterol | Hexoprenaline | Procaterol |
| Ibuterol | Pirbuterol | Salmeterol | Tulobuterol |
| Reproterol | Salbutamol | Sulfonterol | Terbutaline |

1-(2-fluoro-4-hydroxyphenyl)-2-[4-(1-benzimidazolyl)-2-methyl-2- butylamino]ethanol, erythro-5'-hydroxy-8'-(1-hydroxy-2-isopropylaminobutyl)-2H-1,4-benzoxazin-3-(4H)-one, 1-(4-amino-3-chloro-5-trifluoromethylphenyl)-2-tert.-butyl-amino)ethanol, 1-(4-ethoxycarbonylamino-3-cyano-5-fluorophenyl)-2-(tert.-butylamino)ethanol.

As anticholinergics:

Ipratropium bromide

Oxitropium bromide

Trospium chloride

N-β-fluorethylnortropine benzilate methobromide

As steroids:

Budesonide

Beclomethasone (or the 17,21-dipropionate)

Dexamethasone-21-isonicotinate

Flunisolide

As antiallergics:

Disodium cromoglycate

Nedocromil

Epinastin

As PAF-antagonists:

WEB 2086 (4-(2-chlorophenyl)-9-methyl-2-[3-(4-morpholinyl)-3-propanon-1-yl]-6H-thieno-[3,2-f][1,2,4]-triazolo[4,3-a][1,4]diazepine)

WEB 2170 (6-(2-chlorophenyl)-8,9-dihydro-1-methyl-8-[(4-morpholinyl)carbonyl]-4H,7H-cyclopenta[4,5]thieno-[3,2-f][1,2,4]triazolo[4,3-a][1,4]diazepine)

The pharmaceutical preparations according to the invention may contain other excipients such as soya lecithin or surface-active substances.

Surprisingly, it has also been found that the addition of an organic or inorganic acid, preferably in conjunction with a complex forming agent, leads to an improvement in the stability (shelf life) of steroid-containing preparations. This has been found particularly useful for pharmaceutical preparations which contain as active substance Flunisolide or the hydrate or hemihydrate thereof or Budenoside, and which contain ethanol as solvent.

Examples of inorganic acids include, for example: hydrochloric acid, sulphuric acid or phosphoric acid; examples of organic acids include ascorbic acid, malic acid, citric acid, tartaric acid, maleic acid, succinic acid, fumaric acid, acetic acid, formic acid, propionic acid, etc.

The amount of acid in the finished pharmaceutical preparation is in every case selected so that the pH of the solution is between 2.0 and 7.0, especially between 3.0 and 4.0.

In a preferred embodiment, the pharmaceutical preparation also contains a complex forming agent. Examples of complex forming agents include EDTA, citric acid, nitrilo triacetic acid and the salts thereof. The quantity of complex forming agent is between 0.1 and 3 mg/100 ml, preferably between 0.2 and 2 mg/100 ml, particularly between 0.9 and 1.1 mg/100 ml, based on the finished pharmaceutical preparation.

The preferred complex forming agent is EDTA (ethylene diamine tetraacetic acid or a salt thereof, such as the disodium salt). A preferred pharmaceutical preparation according to the present invention contains 1.667% Flunisolide in the ethanol (96% v/v) as solvent, which contains 0.01% (v/v) EDTA as complex forming agent and is adjusted by the addition of acid to a pH of between 3.0 and 4.0.

Examples of steroids which may be used as an active substance in the pharmaceutical preparation according to the invention are:

| | |
|---|---|
| Seratrodast | Mycophenolate mofetil |
| Pranlukast | Zileuton |
| Butixocort | Budesonide |
| Deflazacort | |
| Fluticasone | Promedrol |
| Mometasone furoate | Tipredane |
| Beclomethasone, Douglas | Icomethasone enbutate |
| Ciclometasone | Cloprednol |
| Fluocortin butyl | Halometasone |
| Deflazacort | Alclometasone |
| Ciclometasone | Alisactide |
| Prednicarbate | Hydrocortisone butyrate |
| Tixocortol pivalate | Alclometasone dipropionate |
| Lotrisone | Canesten-HC |
| Deprodone | Fluticasone propionate |
| Methylprednisolone-Aceponate | Halopredone acetate |
| Mometasone | Mometasone furoate |
| Hydrocortisone aceponate | Mometasone |
| Ulobetasol propionate | Aminoglutethimide |
| Triamcinolone | Hydrocortisone |
| Meprednisone | Fluorometholone |
| Dexamethasone | Betamethasone |
| Medrysone | Fluclorolone acetonide |
| Fluocinolone acetonide | Paramethasone acetate |
| Deprodone Propionate | Aristocort diacetate |
| Fluocinonide | Mazipredone |
| Difluprednate | Betamethasone valerate |
| Dexamethasonisonicotinate | Beclomethasone dipropionate |
| Fluocortoloncapronate | Formocortal |
| Triamcinolon hexacetonide | Cloprednol |
| Formebolone | Clobetason |
| Endrisone | Flunisolide |
| Halcinonide | Fluazacort |
| Clobetasol | Hydrocortisone-17-butyrate |
| Diflorasone | Flucortin |
| Amcinonide | Betamethasone dipropionate |
| Cortivazol | Betamethasone adamantoate |
| Fluodexan | Triiostane |
| Budesonide | Clobetasone |
| Demetex | Trimacinolon Benetonide |

9α-chloro-6α-fluoro-11β,17α-dihydroxy-16α-methyl-3-oxo-1,4-androstadiene-17β-carboxylic acid methylester-17-propionate.

Table 1 shows a comparison of a deposition study which was carried out on the one hand with a standard commercial metering aerosol Inhacort® (Flunisolide, dichloromathane, trichlorofluoromethane, cryofluoran, sorbitane triolate)= MDI, and on the other hand with the pharmaceutical preparation according to the invention containing Flunisolide in 96% (v/v) ethanol, which was carried out with a nebuliser as in the above-mentioned PCT Application WO 91/14468 (BINEB®; technical data: volume of drug preparation administered 15 µl, pressure approx. 300 bar, 2 jets squeezed out of two nozzle openings measuring 5×8 µm).

TABLE 1

Deposition study

| | BINEB ® | MDI |
|---|---|---|
| Lung (%) | 39.7 (9.9) | 15.3 (5.1) |
| Mouthpiece (%) | 39.9 (9.4) | 66.9 (7.1) |
| Exhaled part (%) | 10.4 (4.9) | 1.4 (1.3) |
| Central lung region (%) | 10.7 (2.5) | 4.5 (1.8) |
| Middle lung region (%) | 14.9 (3.6) | 5.4 (1.9) |
| Peripheral lung region (%) | 14.1 (4.3) | 5.4 (1.4) |
| Peripheral zone/central zone ratio | 1.3 (0.2) | 1.3 (0.2) |

The Table clearly shows the advantage of the pharmaceutical preparation according to the invention which was administered with the nebuliser described.

EXAMPLES

Flunisolide hemihydrate-6α-fluoro-11β,16α,17α,21-tetrahydropregna-1,4-diene-3,20-16 acetonide hemihydrate has a molecular weight of 442.5. When used in BINEB, 250 µg of Flunisolide are dissolved, per dose, in 15 µl of solution so as to give a concentration of 1.667% g/100 ml).

96% ethanol is used as solvent. In addition, the finished pharmaceutical preparation contains 1 mg/100 ml of disodium-EDTA. The pH value of the pharmaceutical preparation is adjusted to pH 4 using 0.1N HCl.

Analogously to the above experiment, formulations were prepared containing Budesonide as active substance.

The following mixtures of pharmaceutical preparations were made up, containing Flunisolide-hemihydrate as active substance.

TABLE II

| Experiment No. | Combination | Ethanol content (v/v) % | pH | Quantity of disodium EDTA in mg/100 ml |
|---|---|---|---|---|
| 1 | 1 | 85 | 3.6 | 0 |
| 2 | A | 96 | 3.6 | 0 |
| 3 | B | 85 | 7.0 | 0 |
| 4 | AB | 96 | 7.0 | 0 |
| 5 | C | 85 | 3.6 | 1 |
| 6 | AC | 96 | 3.6 | 1 |
| 7 | BC | 85 | 7.0 | 1 |
| 8 | ABC | 96 | 7.0 | 1 |

The Flunisolide-hemihydrate content was 1,666.7 mg/100 ml. The pH of the solution was adjusted using 1N HCl and was determined using a pH meter, pH 1162 Radiometer Copenhagen. The samples were transferred into 5 ml glass ampoules and stored at 80° C. away from light. The combination AC showed the lowest amount of decomposition product after 30 days' storage.

Further examples of formulations which additionally contain disodium EDTA as complex forming agent are shown in Table III.

TABLE III

| Ingredients | I Amount in mg/100 ml | II Amount in mg/100 ml | III Amount in mg/100 ml | IV Amount in mg/100 ml |
|---|---|---|---|---|
| Flunisolide hemihydrate | 1667 | 1667 | 1667 | 1667 |
| Disodium EDTA | 1 | 1 | 1 | 1 |
| 0.1 N HCl | ad pH 3.6 | ad pH 3.2 | ad pH 4.0 | ad pH 3.6 |
| Menthol | — | — | — | 667 |
| Ethanol 96% | ad 100 ml | ad 100 ml | ad 100 ml | ad 100 ml |

The adjuvant menthol was added in order to mask the bitter flavour of the steroid where necessary.

The formulations described above were packaged in 5 ml glass ampoules and stored at 80° C. The preferred preparation, on account of the small amount of decomposition product, is preparation III.

Table IV shows some examples of formulations for Budenoside.

TABLE IV

| Ingredients | I Amount in mg/100 ml | II Amount in mg/100 ml | III Amount in mg/100 ml | IV Amount in mg/100 ml | V Amount in mg/100 ml |
|---|---|---|---|---|---|
| Budesonide | 1333 | 1333 | 1333 | 1333 | 1333 |
| Disodium EDTA | 1 | — | 1 | 1 | — |
| 0.1 N HCl ad pH | 3.2 | 3.2 | 3.6 | 4.0 | 4.0 |
| Ethanol 96% ad | 100 | 100 | 100 | 100 | 100 |

After 3 months' storage at 80° C. in sealed glass ampoules the amount of decomposition product was determined by HPLC. Formulations IV and V showed the smallest amount of decomposition product.

What is claimed is:

1. A stable pharmaceutical budesonide aerosol solution with a pH between 2.0 and 7.0 in which the budesonide is dissolved in a water/ethanol mixture, which mixture optionally includes an alcohol selected from the group consisting of isopropanol and propylene glycol and wherein the stable pharmaceutical budesonide solution comprises 0.001% to 5% by weight of budesonide.

2. The stable pharmaceutical budesonide aerosol solution of claim 1, with a pH between 3.2 and 4.5.

3. The stable pharmaceutical budesonide aerosol solution of claim 1, with a pH between 3.0 and 4.0.

4. The stable pharmaceutical budesonide aerosol solution of claim 1, which further comprises disodium ethylenediaminetetraacetic acid.

5. The stable pharmaceutical budesonide aerosol solution of claim 1, which further comprises between 0.1 and 3 mg/100 ml of disodium ethylenediaminetetraacetic acid.

6. The stable pharmaceutical budesonide aerosol solution of claim 1, which comprises 0.01% to 2% by weight of budesonide.

7. The stable pharmaceutical budesonide aerosol solution of claim 1, with a pH between 2.0 and 7.0 comprising 0.001 to 5% by weight of budesonide and between 0.1 and 3 mg/100 ml of disodium ethylenediaminetetraacetic acid.

8. The stable pharmaceutical budesonide aerosol solution of claim 7, with a pH between 3.2 and 4.5.

9. The stable pharmaceutical budesonide aerosol solution of claim 7, with a pH between 3.0 and 4.0.

10. The stable pharmaceutical budesonide aerosol solution of claim 7, which comprises 0.01% to 2% by weight of budesonide.

11. The stable pharmaceutical budesonide aerosol solution of claim 1, wherein the ethanol concentration is at least 70% (v/v).

12. The stable pharmaceutical budesonide aerosol solution of claim 4, wherein the ethanol concentration is at least 70% (v/v).

13. The stable pharmaceutical budesonide aerosol solution of claim 5, wherein the ethanol concentration is at least 70% (v/v).

14. The stable pharmaceutical budesonide aerosol solution of claim 7, wherein the ethanol concentration is at least 70% (v/v).

15. The stable pharmaceutical budesonide aerosol solution of claim 10, wherein the ethanol concentration is at least 70% (v/v).

16. The stable pharmaceutical budesonide aerosol solution of any of claim 1, wherein the alcohol is ethanol at a concentration of at least 85% (v/v).

17. The stable pharmaceutical budesonide aerosol solution of claim 4, wherein the ethanol concentration is at least 85% (v/v).

18. The stable pharmaceutical budesonide aerosol solution of claim 5, wherein the ethanol concentration is at least 85% (v/v).

19. The stable pharmaceutical budesonide aerosol solution of claim 6, wherein the ethanol concentration is at least 85% (v/v).

20. The stable pharmaceutical budesonide aerosol solution of claim 10, wherein the ethanol concentration is at least 85% (v/v).

21. The stable pharmaceutical budesonide aerosol solution of claim 1, wherein the ethanol concentration is 96% (v/v).

22. The stable pharmaceutical budesonide aerosol solution of claim 4, wherein the ethanol concentration is 96% (v/v).

23. The stable pharmaceutical budesonide aerosol solution of claim 5, wherein the ethanol concentration is 96% (v/v).

24. The stable pharmaceutical budesonide aerosol solution of claim 6, wherein the ethanol is 96% (v/v).

25. The stable pharmaceutical budesonide aerosol of claim 10, wherein the ethanol concentration if 96% (v/v).

26. A process for producing a stable pharmaceutical budesonide-containing aerosol solution with a pH between 2.0 and 7.0 which comprises dissolving the budesonide in a water/ethanol mixture, which optionally contains an alcohol selected from the group consisting of isopropanol and propylene glycol, and adjusting the pH of the budesonide solution to value between 2.0 and 7.0.

27. The process of claim 26, wherein the pH between 3.2 and 4.5.

28. The process of claim 26 wherein the pH is between 3.0 and 4.0.

29. The process of claim 26, which further comprises adding thereto disodium ethylenediaminetetraacetic acid.

30. The process of claim 26, wherein the solution comprises 0.001 to 5% budesonide and between 0.1 and 3 mg/ml of disodium ethylenediaminetetraacetic acid.

31. The process of claim 26, wherein the solution comprises 0.01 to 2% budesonide and between 0.1 and 3 mg/ml of disodium ethylenediaminetetraacetic acid.

32. The process of claim 26, wherein the ethanol concentration is at least 70% (v/v).

33. The process of claim 29, wherein the ethanol concentration is at least 70% (v/v).

34. The process of claim 30, wherein the ethanol concentration is at least 70% (v/v).

35. The process of claim 31, wherein the ethanol concentration is at least 70% (v/v).

36. The process of claim 26, wherein the ethanol concentration is at least 85% (v/v).

37. The process of claim 29, wherein the ethanol concentration is at least 85% (v/v).

38. The process of claim 30, wherein the ethanol concentration is at least 85% (v/v).

39. The process of claim 31, wherein the ethanol concentration is at least 85% (v/v).

40. The process of claim 26, wherein the ethanol concentration is at least 96% (v/v).

41. The process of claim 29, wherein the ethanol concentration is at least 96% (v/v).

42. The process of claim 30, wherein the ethanol concentration is at least 96% (v/v).

43. The process of claim 31, wherein the ethanol concentration is at least 96% (v/v).

* * * * *